United States Patent [19]

Stock et al.

[11] Patent Number: 4,885,255

[45] Date of Patent: Dec. 5, 1989

[54] IMMUNOCHEMICAL PROCESS AND REAGENT FOR THE DETERMINATION OF A POLYVALENT ANTIGEN IN A LIQUID SAMPLE

[75] Inventors: Werner Stock, Gräfelfing; Manfred Baier, Seeshaupt, both of Fed. Rep. of Germany; Klaus P. Kaspar, Asuncion, Paraguay; Peter Kirch, Weilheim, Fed. Rep. of Germany

[73] Assignee: Boehringer Mannheim GmbH, Mannheim-Waldhof, Fed. Rep. of Germany

[21] Appl. No.: 173,779

[22] Filed: Mar. 28, 1988

[30] Foreign Application Priority Data

Apr. 28, 1987 [DE] Fed. Rep. of Germany ....... 3714147

[51] Int. Cl.$^4$ .................. C01N 33/563; C01N 33/053; C01N 33/544; C01N 33/541
[52] U.S. Cl. .................................... 436/512; 436/513; 436/530; 436/540; 436/548; 436/824
[58] Field of Search ............... 436/512, 530, 540, 548, 436/824

[56] References Cited

U.S. PATENT DOCUMENTS

| | | | |
|---|---|---|---|
| 4,376,110 | 3/1983 | David | 436/540 X |
| 4,433,059 | 2/1984 | Chang | 436/540 X |
| 4,624,930 | 11/1986 | Tanswell | 436/512 X |
| 4,657,853 | 4/1987 | Fregtag | 436/512 X |
| 4,659,678 | 4/1987 | Forrest | 436/531 X |

*Primary Examiner*—Robert J. Hill, Jr.
*Assistant Examiner*—Karen I. Kruper
*Attorney, Agent, or Firm*—Felfe & Lynch

[57] ABSTRACT

The present invention provides a process for the quantitative determination of a polyvalent antigen by incubation with three different receptors of which the first (R1) and the third (R3) are present in liquid phase and are bindable with the antigen, the second receptor (R2) is present in solid phase and is bindable with receptor (R1), and receptor (R3) carries a label and does not cross-react with (R1) and (R2), separation of the solid phase from the liquid phase and measurement of the label in one of the phases, wherein a first receptor (R1) is used which consists of at least two antibody molecules or antibody molecule fragments bound with one another, at least one of which binds specifically with the antigen to be determined.

The present invention also provides a reagent for the quantitative determination of a polyvalent antigen containing three receptors (R1, R2 and R3) of which (R1) and (R3) are soluble and bindable with the antigen, (R3) is labelled and does not cross-react with (R1) and (R2), wherein (R1) consists of at least two antibody molecules or antibody molecule fragments bound with one another, at least one of which binds specifically with the antigen to be determined.

21 Claims, 3 Drawing Sheets

IMMUNOCHEMICAL PROCESS AND REAGENT FOR THE DETERMINATION OF A POLYVALENT ANTIGEN IN A LIQUID SAMPLE

The present invention is concerned with an immunochemical process and reagent for the determination of a polyvalent, i.e. at least bifunctional antigen in a liquid sample.

The sensitive determination of polyvalent antigens (peptides, proteins) with the use of two antibodies which are directed against different antigen determinants is known, for example, from J. Clin. Chem. Clin. Biochem., 18, 197-208/1980. Numerous variants of this process have become known, for example from Federal Republic of Germany Patent Specification No. 34 00 027. According to this Patent Specification, for the determination of the polyvalent antigen, an incubation is carried out with three different receptors, of which the first and third are present dissolved in liquid phase and are bindable with the antigen, whereas the second receptor is present in solid phase and is bindable with the first receptor and the third receptor is labelled and does not cross-react with the first and second receptor. By means of the incubation of the antigen to be determined with the three receptors, which can be carried out in various ways, there is finally obtained a sandwich structure bound to the solid phase in which the second receptor bound to the solid phase binds the first receptor, the latter again binds the antigen and the antigen finally binds the labelled third receptor.

A disadvantage of the processes and reagents based on this principle lies in the unsatisfactory stability of the reagent used therefor. By stability there is hereby to be understood the constancy of the calibration curve (signal/concentration of the analytes) over a comparatively long period of time. The result of the unsatisfactory stability is that the calibration curves of the freshly prepared reagents do not agree with the calibration curves of the stored reagent. As a rule, it is observed that, with increasing storage, the calibration curve becomes flatter. The reasons for this are not known.

It is an object of the present invention so to improve a process and a reagent of the above-described kind that the stability of the calibration curve is obtained over a longer period of time than previously so that, in other words, the dependability of the double antibody solid phase assay (DASP) is improved.

Thus, according to the present invention, there is provided a process for the quantitative determination of a polyvalent antigen by incubation with three different receptors of which the first (R1) and the third (R3) are present dissolved in liquid phase and are bindable with the antigen, the second receptor (R2) is present in solid phase and is bindable with (R1) and (R3) carries a label and does not cross-react with (R1) and (R2), separation of the solid phase from the liquid phase and measurement of the labelling in one of the phases, wherein a first receptor (R1) is used which consists of at least two antibody molecules or antibody molecule fragments bound with one another, at least one of which binds specifically with the antigen to be determined.

Surprisingly, we have found that, in the case of the use of an oligomeric or polymeric first receptor (R1), there is obtained a substantial improvement of the stability of the process and of the reagent.

As receptors in the scope of the present invention, there are used specifically bindable substances, especially either specifically bindable complete antibodies, which can be polyclonal or monoclonal, antibody fragments thereof or conjugates of antibodies or antibody fragments with haptens or antigens. Monoclonal antibodies are preferably used.

In the following explanations, the term "antibody" or "antibody molecule" is to be understood to mean not only the complete antibodies but also bindable fragments thereof which are known to the expert. By a polyvalent antigen, there is here to be understood an antigen with several antigenic determinants.

The two receptors R1 and R2 form a substance pair specifically bindable with one another. Thus, for example, the receptor R2 can be in immunoglobulin or protein A directed against the receptor R1 when the receptor R1 is an antibody. Furthermore, the receptor R2 can be avidin, streptavidin or biotin when the receptor R1 is a biotinylated antibody or an antibody provided with avidin. Further substance pairs can be used and are known to the expert.

Preferably, the first receptor (R1) consists of identical antibodies or bindable fragments thereof cross-linked with one another, which can be monoclonal or polyclonal. The individual antibody molecules are thereby bound with one another by bivalent or polyvalent linkers (bridge formers). The cross-linking with bivalent linkers is preferred since they permit a simpler control of the "degree of polymerisation" of the receptor. However, the action according to the present invention is also achieved with polyvalent linkers.

In order that, due to the linker, the binding points of the individual antibodies of which the receptor (R1) consists, are not blocked, preferably not more than 10 linkers per antibody molecule should be bound, there preferably being 2 to 5 linkers per antibody molecule. Depending upon the reactivity of the binding functions of the linker, there are obtained these preferred coupling products when linker and antibody are used in a molar ratio of about 1:1 to 50:1 for the cross-linking. those compounds which have reactive groups which are able to react in aqueous solution with the functional groups of proteins with the formation of a covalent bond. A large number of bifunctional and polyfunctional linkers appropriate for this purpose are known to the expert. Typical examples in the scope of the present invention of well-suited homo- or hetero-bifunctional and trifunctional linkers are set out in the following Table 1:

TABLE 1

| abbreviation | chemical designation |
|---|---|
| SPDP | N—succinimidyl 3-(2-pyridyldithio)-propionate |
| EADB | ethyl 4-azidophenyl-1,4-dithiobutyrimidate hydrochloride |
| FNPA | 4-fluoro-3-nitrophenylazide |
| HSAB | N—hydroxysuccinimidyl-4-azidobenzoate |
| MABI | methyl-4-azidobenzoimidate hydrochloride |
| MBS | m-maleimidobenzoyl-N—hydroxysuccinimide ester |
| NHS—ASA | N—hydroxysuccinimidyl-4-azidosalicylic acid |
| MHS | m-maleimidohexanoyl-N—hydroxysuccinimide ester |
| PNP—DTP | p-nitrophenyl-2-diazo-3,3,3-trifluoro-propionate |
| SADP | N—succinimidyl (4-azidophenyl)-1,3'-dithiopropionate |
| SAND | sulphosuccinimidyl 2-(m-azido-o-nitrobenzimido)-ethyl-1',3'-dithiopropionate |
| SANPAH | N—succinimidyl 6-(4'-azido-2'-nitrophenylamino)-hexanoate |

TABLE 1-continued

| abbreviation | chemical designation |
|---|---|
| SASD | sulphosuccinimidyl 2-(p-azidosalicyl-amido)-ethyl-1,3'-dithiopropionate |
| SIAB | N—succinimidyl (4-iodoacetyl-amino-benzoate |
| SMCC | succinimidyl 4-(N—maleimidoethyl)-cyclohexane-1-carboxylate |
| SMPB | succinimidyl 4-(p-maleimidophenyl)-butyrate |
| DSS | disuccinimidyl suberate |
| DMS | dimethyl suberimidate |
| Traut's reagent | 2-iminothiolane |
| — | 2,4,6-trichloro-s-triazine |

For carrying out the cross-linking, a solution of the antibodies to be bound with one another can be mixed with the linker molecules under conditions which lead directly to the cross-linking. In this case, the extent of the cross-linking is controlled by the amount of linker added thereto.

The cross-linking preferably takes place in such a manner that half of the antibodies to be bound with one another are reacted with a first linker under conditions in which only one of the functions of the linker lead to binding with the antibody. In an analogous way, the other half of the antibodies to be cross-linked are reacted with the second linker. The two antibody derivatives thus obtained are reacted with one another. There is hereby preferably used a molar ratio of the antibody derivatives to be connected with one another of from 2:1 to 1:2, a ratio of about 1:1 being especially preferred.

The receptor (R1) preferably contains 2 to 20 antibody molecules and especially preferably 4 to 12 antibody molecules.

Apart from the case already explained above of the receptor (R1) composed of a single type of antibody (homologous antibodies present as oligomer or polymer), the receptor (R1) can also be composed of two different antibodies, each of which display a good, specific bindability towards the antigen to be determined and towards the receptor (R2). In this case, the preparation of the complete receptor (R1) takes place by the above-described preferred method of the individual derivation of the two different antibodies and subsequent reaction of the two derivatives with one another.

For use in the scope of the present invention, a receptor (R1) is preferred which, with regard to its degree of polymerization or to the number of antibody molecules contained therein, displays a composition which is as uniform as possible. This can be activated in a simple way by chromatographic pre-purification.

As receptor (R2), there is used a receptor bound to an insoluble phase which is bindable with the receptor (R1). (R2) is preferably an antibody in the meaning of the above definition. (R2) is either bindable with a part of the receptor (R1) composed of homologous antibodies or, in the case of heterogeneously composed receptors (R1), with those components which display the lesser affinity with the antigen to be determined. The receptor (R2) is preferably directed against the Fc part of an antibody molecule in receptor (R1). A receptor (R2) can also be used which is generally directed against the Fc part of immunoglobulin.

Like the receptor (R1), the third receptor (R3) is bindable with the polyvalent antigen to be determined. It can obtain a polyclonal or monoclonal antibody. If it is a monoclonal antibody, then it is so chosen that it bonds to an epitope different from (R1). This can be achieved in a simple way in that there is used not only in (R1) but also in (R3) in each case a monoclonal antibody which is bindable with the polyvalent antigen to be determined, these monoclonal antibodies thereby recognising different antigenic determinants. This has the advantage that both antibodies can originate from the same experimental animal.

Furthermore, the receptor (R3) carries a labelling. The labelling can be an enzyme, a radio-active substance, an isotope or a fluorescing or chemiluminescing substance, the determination of which is carried out by methods well known to the expert. Thus, for example, when the labelling takes place with an enzyme, such as peroxidase or $\beta$-galactosidase, the activity of this enzyme is measured in the way generally known therefor in that a known detection reagent for this labelling enzyme, for example a colour reagent, is added thereto and measured either in the presence of the solid phase or after separation. The measured enzyme activity is then a measure for the amount of polyvalent antigen to be determined.

The present invention also provides a reagent for the quantitative determination of a polyvalent antigen containing three receptors (R1, R2 and R3), of which (R1) and (R3) are soluble and bindable with the antigen, (R3) is labelled and does not cross-react with (R1) and (R2), wherein (R1) consists of at least two antibody molecules or antibody molecule fragments bound together, at least one of which binds specifically with the antigen to be determined.

The preferred embodiments of this reagent have already been explained hereinbefore in detail in connection with the determination process and apply analogously for the composition of the reagent.

By means of the present invention, there is achieved an improvement of the stability of the reagents for heterogeneous immunoassays, such as the double antibody sandwich process, especially with regard to the constancy of the calibration curve over a comparatively long period of time. Due to the improved constancy of the calibration curve achieved, the dependability of the determination is increased.

The following Examples and Figures are given for the purpose of illustrating the present invention:

DETAILED DESCRIPTION OF PREFERRED EMBODIMENTS

EXAMPLE 1

Figure 1:
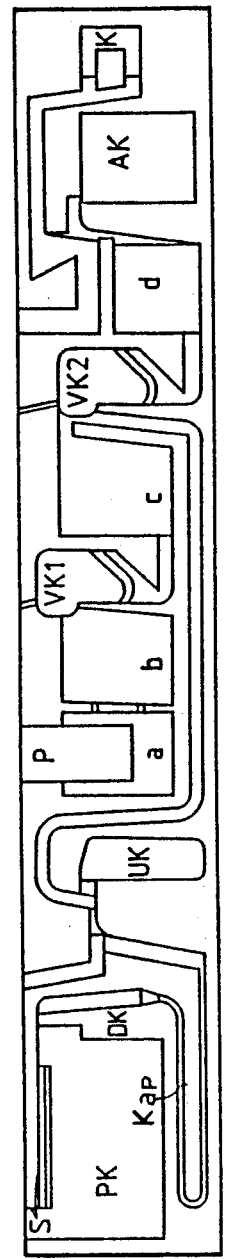
FIG. 1 shows a rotor insert element according to DE-AS 34 25 008.2.

Determination of alfa fetal protein.

1. Preparation of the reagents 1.1 Buffer I:

50 mMole/liter potassium phosphate buffer (pH 6.0), prepared by mixing 50 mMole/liter dipotassium hydrogen phosphate solution and 50 mMole/liter monopotassium dihydrogen phosphate solution until the pH value of 6.0 is achieved.

1.2 Buffer II:

Buffer II is prepared like Buffer I but with the difference that a pH value of 7.5 is adjusted and that the buffer additionally contains 10 g./liter of bovine serum albumin and 150 mMole/liter sodium chloride.

1.3 Receptor (R1') (Non-cross-linked anti-AFP antibody).

As receptor (R1'), there is used a monoclonal mouse anti-AFP antibody of the subclass $IgG_{2a}$ (ECACC 87041002). The ascites fluid containing this antibody is mixed with ammonium sulphate to 1.8 M. The precipitate is taken up in a buffer of 15 mM sodium phosphate (pH 7.0) and 50 mM sodium chloride. The solution thus obtained is subjected to a passage over DEAE-cellulose. The eluate so obtained containing antibodies bindable with AFP is subsequently freeze-dried.

1.4 Receptor (R1) (cross-linked anti-AFP antibody)

1.4.1 Derivation of the AFP-specific antibody 10 mg of receptor (R1') (monoclonal mouse antiAFP antibody; see 1.3) are dissolved in 1 ml. 0.1 M sodium phosphate buffer (pH 7.5). After the addition of 0.1 mg. succinimidyl 3-(2-pyridyl dithio)-propionate (SPDP), there follows a reaction period of 1 hour at 25° C. After adjustment of the pH value with acetic acid to 4.5 and the addition of 8 mg. dithiothreitol, there follows a further reaction period of 20 minutes at 25° C. The product is desalinated by passage over 10 ml. ACA-202 gel (producer: LKB, Sweden) in a chromatography column in 10 mM potassium phosphate buffer (pH 6.15) with 25 mM sodium chloride and 10 mM magnesium chloride. The product is concentrated by means of a commercially available ultrafiltration apparatus (Amicon Corp. U.S.A.) to a protein concentration of 14 mg./ml.

1.4.2 Derivation of the cross-linking partner 10 mg. of a monoclonal mouse anti-hCG-antibody of the sub-class $IgG_1$ (ECACC 87041001) (preparation as described under 1.3) are derivatised according to a known process (see Ishikawa et al., J. Immunoassay, 4, 209 et seq./1983) with N-succinimidyl 4-(N-maleinimidomethyl)-cyclohexane-1-carboxylate (SMCC). Desalination and concentration are carried out as described under 1.4.

1.4.3. Conjugation 10 mg. each of the antibody derivatives from 1.4.1 and 1.4.2 are reacted together at pH 7.0 and at 25° C. for 1.5 hours. The reaction is stopped by the addition of cysteine to 1 mM (30 minutes, 25° C.) and subsequently iodoacetamide (1 hour, 25° C.). The product is desalinated as described in 1.4.1 and concentrated.

1.5 Labelled receptor (R3) solution

As receptor (R3), there is used a polyclonal mouse anti-AFP antibody which, after an immunosorptive purification as described in 1.3, is further treated. The complete antibody is split into Fab fragments in known manner according to the method of R.R. Porter (Biochem. J., 73, 119/1959). The Fab fragments thus obtained are coupled with $\beta$-galactosidase according to Ishikawa et al. (J. of Immunoassay, 4, 209-327/1983). The receptor (R3) solution is diluted with buffer II to a concentration of 500 mU/ml. (measured with o-nitrophenyl-$\beta$-galactoside at 37° C.).

1.6. Receptor (R2) solution

Sheep anti-mouse Fc$\gamma$-antiserum is mixed with ammonium sulphate to 1.8 M. The precipitate obtained is taken up in a buffer of 15 mM sodium phosphate (pH 7.0) and 50 mM sodium chloride. The solution thus obtained is subjected to a passage over DEAE-cellulose. The eluate containing the specific antibody is diluted with buffer I to a protein concentration of 50 $\mu$g./ml.

1.7. Substrate solution

| | |
|---|---|
| chlorophenol red $\beta$-galactoside (prepared according to Federal Republic of Germany Patent Specification No. 33 45 748) | 5 mmole/liter (3.05 g./l.) |
| HEPES | 70 mmole/liter (16.7 g./l.) |
| sodium chloride | 154 mmole/liter (9 g./l.) |
| bovine serum albumin | 0.3% (3 g./l.) |
| Tween 20 | 0.2% (2 g./l.) |
| pH (adjusted with aqueous sodium hydroxide solution) | 7.25 |

2. Preparation of reagent carriers (pad of paper or fleece material)

2.1. Reagent carrier 1' (comparative; with non-cross-linked receptor (R1')).

40 $\mu$l. of a solution which, per liter, contains 100 mMole sodium phosphate (pH 7.3, 37° C.), 2 mMole magnesium chloride, 9 g. sodium chloride, 5 g. bovine serum albumin, 5 mg. anti-AFP monoclonal antibodies from mice (receptor R1') (200 ng. AB/test), 1000 U anti-AFP antibody (mouse) Fab fragment-$\beta$-galactosidase conjugate (receptor R3 solution; activity determined with o-nitrophenyl-$\beta$-D-galactoside at 37° C.), is dropped on to a fleece which consists of a commercially available polyester paper. Subsequently, it is dried at ambient temperature. Until used, these fleece are stored at 4° C. and at a relative humidity of 20%.

2.2. Reagent carrier 1 (according to the present invention; with cross-linked receptor (R1)).

The preparation takes place as for reagent carrier 1' except for the difference that, instead of the non-cross-linked monoclonal anti-AFP antibody (receptor (R1')), there is used a cross-linked, monoclonal anti-AFP antibody from mice (receptor (R1)).

2.3. Reagent carrier 2.

On to a cellulose fleece are fixed, according to the cyanogen bromide activation process (see Federal Republic of Germany Patent Specification No. 17 68 512), sheep antibodies against the Fc$\gamma$ part of the mouse antibodies (receptor R3 solution), whereby, per g. of fibre material, there are available 10 $\mu$g. of antibody for the fixing. Uncoupled antibody is removed by washing and the fleece is gently dried at ambient temperature. The fleece thus obtained is stored analogously to reagent carrier 1.

3. Carrying out the determination.

The determination with the help of these two reagent carriers 1 and 2 and 1' and 2, respectively, is carried out with the device for carrying out analytical determinations described in Federal Republic of Germany Patent Specification No. 34 25 008 (FIG. 1).

This describes a rotor insert element for a centrifugal automatic analyzer comprising a formed body which contains a plurality of reagent fields in combination, each of which contains an absorbent carrier material impregnated with a particular reagent, at least one mixing valve chamber and a measurement chamber which together form a sample liquid transport path which runs radially outwardly when the insert element is fixed on to the rotor and also a further chamber for the reception of a liquid and a transport path which leads from this chamber to the measurement arrangement and is at least partly identical with the sample liquid transport path.

The sample liquid transport path thereby passes from a sample application chamber (P) via a chamber (a) filled with absorbent material containing buffer, a chamber (c) and a first valve chamber (Vk1) arranged between the chambers (a) and (c) to a second valve chamber (Vk2) and from this, via chamber (d) and via a reception chamber (AK) to the measurement chamber (K). Additional chamber (b) is shown, but is not used in the experiments described herein. For the reception of a further liquid, there is provided a substrate chamber (PK) having an entry port (S) constructed as a pump chamber which is connected via a dosaging device, consisting of a dosaging chamber (DK) and capillary (Kap), and an overflow chamber (UK) with a second valve chamber (Vk2). FIG. 1 of the drawings of the above-mentioned German Patent Specification shows schematically the rotor insert element used.

Reagent carrier 1 or 1' is placed on field c of the rotor insert element and reagent carrier 2 on field d. 40 μl. of a sample diluted 1:3 v/v with a 0.9% aqueous solution of sodium chloride is thereby pipetted through an opening on the upper edge directly on to the field a. 270 μl. of substrate solution are pipetted into chamber PK. By means of an appropriate centrifuging program, in which high speeds of rotation alternate with stopping, the sample and substrate solution are then conveyed in the direction of the separation matrix and cuvette.

In the course of the program, the receptors (R3) and (R1) or (R1') are thereby eluted by the sample liquid from field c and the homogeneous mixture subsequently brought to reaction. On field d, the complexes formed are bound on to the receptor (R2). The transfer of the sample from field c to field d takes place within a very short period of time.

The substrate solution is divided up into portions by the dosaging chamber (DK), the first of which serves for washing out excess, non-complexed conjugate. The β-galactosidase activity bound to d via complex formation is proportion to the amount of AFP contained in the sample or to the sample blank value. This activity is determined with a further portion of substrate, the substrate thereby being reacted in a 5 minute reaction to give coloured products. The colour formed and the further colour development per minute in the liquid phase are measured in the cuvette at 576 nm.

Under these conditions, there are determined calibration lines not only with unstressed rotor insert elements but also with rotor insert element stressed for 3 weeks at 35° C., including their regent carriers. The results given in the following Table 2 are thereby obtained:

TABLE 2

| AFP concentration (IU/ml) | results in extinction units in the case of the use of | | | |
|---|---|---|---|---|
| | non-cross-linked receptor R1' | | cross-linked receptor R1 | |
| | 0 | 70 | 0 | 70 |
| (a) insert element with reagent carriers without temperature stressing | 0.303 | 4.955 | 0.327 | 5.702 |
| (b) insert element with reagent carriers stressed for 3 weeks at 35° C. | 0.302 | 3.652 | 0.301 | 4.970 |
| (c) calibration curve[1] stability after | — | 72% | — | 87% |

TABLE 2-continued

| AFP concentration (IU/ml) | results in extinction units in the case of the use of | | | |
|---|---|---|---|---|
| | non-cross-linked receptor R1' | | cross-linked receptor R1 | |
| | 0 | 70 | 0 | 70 |
| stressing | | | | |

[1]calculation of the calibration curve stability:

$$\frac{\text{signal difference (0/70 IU/ml AFP) insert element stressed (b)}}{\text{signal difference (0/70 IU/ml AFP) insert element without stressing (a)}} \times 100$$

EXAMPLE 2

2.1. Preparation of the reagent 2.1.1. Receptor (R1') (comparison; non-cross-linked anti-human luteinizing hormone (hLH) antibody).

As receptor (R1') there is used a monoclonal mouse anti-hLH antibody of the sub-class $IgG_1$ (NCACC 84122001). ammonium sulphate to 1.8 M. The precipitate obtained is taken up in a buffer of 15 mM sodium phosphate (pH 7.0) and 50 mM sodium chloride. The solution thus obtained is subjected to a passage over DEAE-cellulose. The so obtained eluate containing antibody bindable with hLH is subsequently freeze dried.

2.1.2. Receptor (R1) (according to the present invention; cross-linked anti-hLH antibody)

In contradistinction to Example 1, in this Example there is used an antibody cross-linked with another identical antibody. For the preparation thereof, the receptor (R1') is derived according to Example 1, 1.4.1 and 1.4.2.

10 mg. amounts of this antibody derivative are reacted together at pH 7.0 and at 25° C. for 1.5 hours. The reaction is stopped by the addition of cysteine to 1 mM (30 minutes, 25° C.) and subsequently iodoacetamide (1 hour, 25° C.). The product is desalinated and concentrated as described in Example 1. 1.4.1.

2.1.3. Labelled receptor (R3) solution (R3) is a conjugate consisting of β-galactosidase and a monoclonal anti-LH antibody Fab fragment. The Fab fragment is obtained in known manner according to R. R. Porter (Biochem. J., 73, 119/1959) by splitting the complete monoclonal anti-LH antibody (NCACC 84122005). The specificity of (R3) is different from that of (R1). (R3) recognizes on the LH molecule different antigenic determinants and can form a sandwich with (R1). Antibody production and conjugate synthesis correspond to Example 1, 1.5.

2.1.4. Other reagents

The other reagents, for example buffers I and II, receptor (R2) solution and substrate solution, are identical to the reagents used in Example 1.

2.2.1. Reagent carrier 1' (with non-cross-linked receptor (R1')).

40 μl. of a solution which, per liter, contains 100 mMole sodium phosphate (pH 7.3; 37° C.), 2 mMole magnesium chloride, 9 g. sodium chloride, 5 g. bovine serum albumin, 10 mg. or 20 mg. anti-hLH monoclonal antibody from mice (receptor R1') (400 ng. AB/test or 800 ng. AB/test), 1000 U anti-hLH antibody (mouse) Fab fragment-β-galactosidase conjugate (receptor R3 solution; activity determined with O-nitrophenyl-β-Dgalactoside at 37° C.), are dropped on to a fleece which consists of a commercially available polyester paper. Subsequently, it is dried at ambient temperature.

These fleece are stored at 4° C. and a relative humidity of 20% until used.

2.2.2. Reagent carrier 1

The production takes place as for reagent carrier 1' except for the different that, instead of receptor (R1'), there is used a receptor (R1) cross-linked with another identical antibody.

2.2.3. Reagent carrier 2

On to a cellulose fleece are fixed, according to the cyanogen bromide activation process (see Federal Republic of Germany Patent Specification No. 17 67 512), sheep antibodies against the Fcγ-part of mouse antibodies (receptor R2 solution), per g. of fibre material there are provided 10 μg. of antibody for the fixing. Uncoupled antibody is removed by washing and the fleece gently dried at ambient temperature. The storage of the so obtained fleece takes place analogously to reagent carrier 1.

3. Carrying out of the determination

Figure 2:
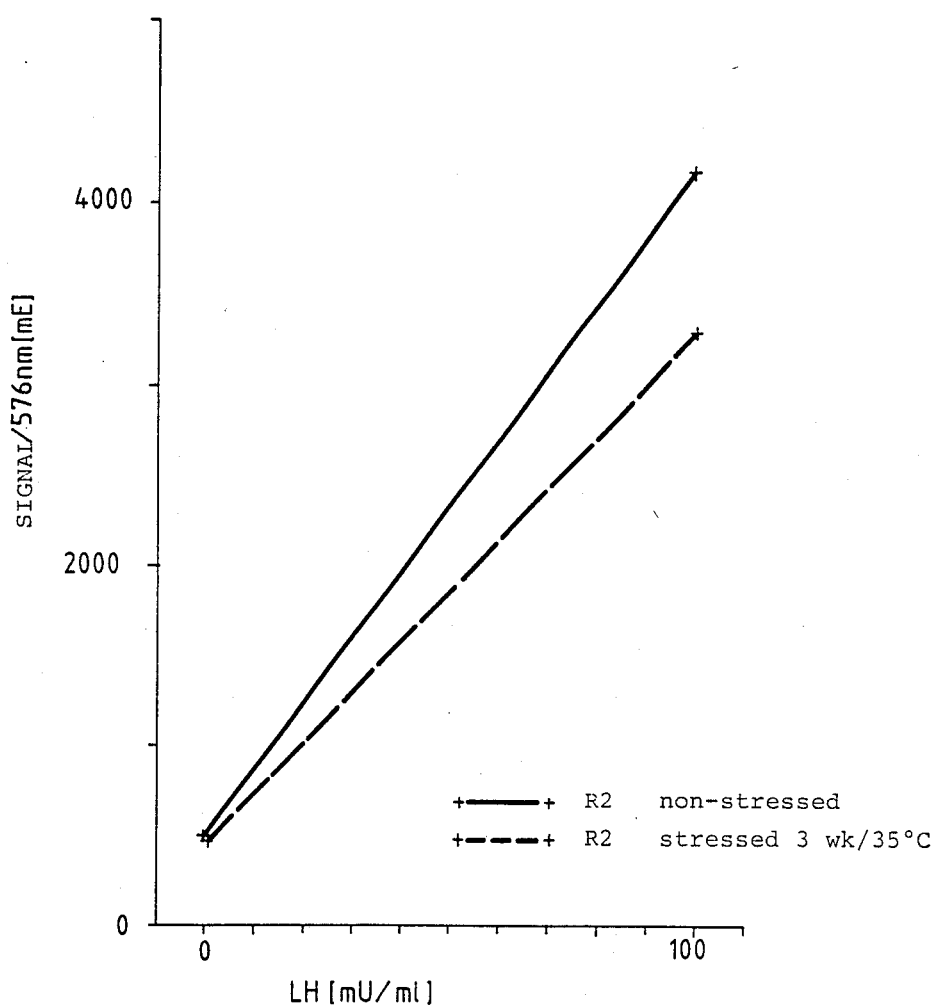
FIG. 2 shows a LH calibration curve with receptor R1' (non-crosslinked).
Figure 3:
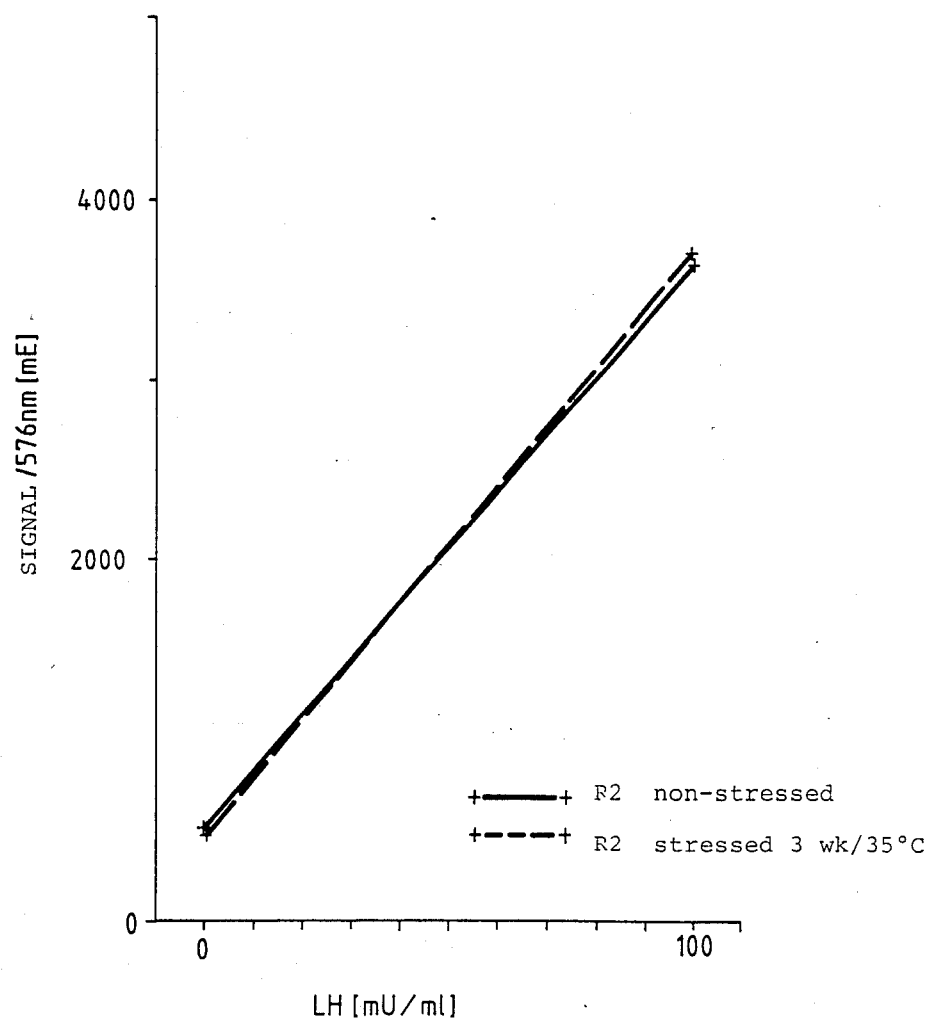
FIG. 3 shows a LH calibration curve with receptor R1 (cross-linked).

The carrying out of the determination takes place analogously to Example 1. FIGS. 2 and 3 of the accompanying drawings show the results obtained in the case of using 400 ng. AB/test in reagent carrier 1' or 1, respectively. The following Table 3 shows the results for 400 and 800 ng. AB/test, respectively.

TABLE 3

|  | non-cross-linked receptor R1' LH-concentration (mU/ml) | | cross-linked receptor R1 LH-concentration (mU/ml) | |
| --- | --- | --- | --- | --- |
|  | 0 | 100 | 0 | 100 |
| A. Results in the case of using 400 ng. receptor R1' or R1 in reagent carrier 1' or 1 respectively. | | | | |
| reagent carrier R2 non-stressed | 487* | 4177 | 510 | 3635 |
| reagent carrier R2 stressed for 3 weeks at 35° C. | 462 | 3288 | 473 | 3699 |
| calibration curve stabilty after stressing** |  | 77% |  | 100% |
| B. Results in the case of using 800 ng. receptor R1' or R1 in reagent carrier 1' or 1 respectively. | | | | |
| reagent carrier 2 non-stressed | 460 | 3430 | 481 | 4184 |
| reagent carrier 2 stressed for 3 weeks at 35°C. | 422 | 2637 | 508 | 4003 |
| calibration curve stability after stressing** |  | 75% |  | 94% |

*All measurements were carried out at λ = 576 nm at a layer thickness of 0.3 cm. and recalculated to a layer thickness of d = 1 cm.
In each case, there is given the average value in milli-extinctions of 4 determinations.
** Calculation of the calibration curve stability:
$$\frac{\text{signal difference (0/100 mU/ml LH) δ stressed}}{\text{signal difference (0/100 mU/ml LH) non-stressed}} \times 100$$

We claim:

1. Process for the quantitative determination of a polyvalent antigen comprising incubating a liquid sample containing said antigen with three different receptors, wherein the first receptor (R1) and the third receptor (R3) are in liquid phase and bind with the polyvalent antigen, and the second receptor (R2) is in solid phase and binds with (R1), wherein (R3) carries a label and does not cross react with (R1) and (R2) to form a solid phase complex of (R2), (R1), antigen and (R3), separating the solid phase from the liquid phase and measuring the label in one of the phases as an indication of said polyvalent antigen, wherein said first receptor either comprises an oligomer of at least two antibody molecules or consists of a oligomer of antibody fragments selected from the group consisting of Fab or (Fab')$_2$ fragments bound together which antibody molecules or antibody fragments all have specificity for the antigen to be determined.

2. Process according to claim 1, wherein (R1) consists of identical monoclonal antibodies cross-linked together.

3. Process according to claim 1, wherein (R1) consists of different monoclonal antibodies cross-linked together.

4. Process according to claim 1, wherein the components of (R1) are bound by di- or polyvalent linkers.

5. Process according to claim 1, wherein said receptor (R1) contains from 2 to 20 antibody molecules or antibody fragments.

6. Process according to claim 1, wherein said receptor (R1)' contains from 4 to 12 antibody molecules or antibody fragments.

7. Process according to claim 1 wherein (R1) is present in a concentration equal to from 0.5 to 1 fold of the concentration of (R2).

8. Process according to claim 1, wherein (R2) binds with the Fc part of an antibody in (R1).

9. Process for the preparation of a receptor (R1) either containing at least two antibodies or consists of a oligomer of antibody fragments selected from the group consisting of Fab and (Fab')$_2$ fragments bound together wherein all of said antibodies or antibody fragments have specificity for an identical antigen comprising reacting from ¼ to ½ of the total amount of each antibody or antibody fragment with a di- or polyvalent linker to provide derivatives of said antibodies or antibody fragments thereof and linking two of said derivatives together under conditions which favor reaction of said linkers to form said receptor (R1).

10. Process according to claim 9, wherein the two derivatives are reacted with one another in a molar ratio of 2:1 to 1:2.

11. Reagent for the quantitative determination of a polyvalent antigen comprising three receptors (R1, R2 and R3) wherein receptor (R1) and receptor (R3) are soluble and bind to the antigen to be determined, wherein receptor (R3) is labelled and does not cross react with receptor (R1) either and receptor (R2), and receptor (R1) comprises at least two antibodies or consists of a oligomer of antibody fragments selected from the group consisting of Fab and (Fab')$_2$ fragments bound together, wherein all of said antibodies or antibody fragments specifically bind with the antigen to be determined, and wherein receptor (R2) is in insoluble form and binds to (R1).

12. Reagent according to claim 11, wherein receptor comprises identical or different monoclonal antibodies cross-linked together.

13. Reagent according to claim 11, wherein (R1) contains from 2 to 20 antibody molecules or fragments thereof.

14. Reagent according to claim 11, wherein receptor (R1) contains from 4 to 12 antibody molecules or fragments thereof.

15. Reagent according to claim 11 wherein receptor (R1) is present in an amount ranging from 0.5 to 1 fold the active amount of (R2).

16. Process of claim 1, wherein R1 comprises identical polyclonal antibodies cross-linked together.

17. Process of claim 1, wherein R1 comprises identical antibody fragments cross-linked together.

18. Process of claim 1, wherein (R1) comprises different polyclonal antibodies cross-linked together.

19. Process of claim 1, wherein (R1) comprises different antibody fragments cross-linked together.

20. Reagent of claim 11 wherein (R1) comprises polyclonal antibodies cross-linked together.

21. Reagent of claim 11, wherein (R1) comprises antibody fragments cross-linked together.

* * * * *

UNITED STATES PATENT AND TRADEMARK OFFICE
CERTIFICATE OF CORRECTION

PATENT NO. : 4,885,255

DATED : December 5, 1989

INVENTOR(S) : Werner Stock, et al.

It is certified that error appears in the above-identified patent and that said Letters Patent is hereby corrected as shown below:

Column 2, line 40: prior to "those" add -- As linkers (bridge builders), there can be used --.

Column 3, line 66: change "obtain" to -- contain --.

Column 8, line 21: prior to "ammonium" insert -- The ascites fluid containing this antibody is mixed with --.

Column 9, line 11: change "1767512" to -- 17 68 512 --.

IN THE CLAIMS

Claim 6, line 2: change "(R1)'" to -- (R1) --.

Claim 9, line 7: change "1/2" to -- 3/4 --.

Claim 12, line 1: after "receptor" add -- (R1) --.

Claim 13, line 1: before "(R1)" insert -- receptor --.

Signed and Sealed this

Twenty-sixth Day of March, 1991

Attest:

HARRY F. MANBECK, JR.

Attesting Officer

Commissioner of Patents and Trademarks